(12) United States Patent
Schulze

(10) Patent No.: US 7,842,037 B2
(45) Date of Patent: Nov. 30, 2010

(54) FLEXIBLE BONE FIXATION DEVICE

(75) Inventor: Dale R. Schulze, Ft. Wayne, IN (US)

(73) Assignee: DuPuy Products, Inc., Warsaw, IN (US)

( * ) Notice: Subject to any disclaimer, the term of this patent is extended or adjusted under 35 U.S.C. 154(b) by 565 days.

(21) Appl. No.: 11/527,951

(22) Filed: Sep. 27, 2006

(65) Prior Publication Data

US 2008/0097432 A1     Apr. 24, 2008

(51) Int. Cl.
    *A61B 17/80* (2006.01)
(52) U.S. Cl. .................. 606/71; 606/70; 606/280; 606/282; 606/284
(58) Field of Classification Search ............ 606/60, 606/70–71, 74, 280–299; 623/17.11–17.16
    See application file for complete search history.

(56) References Cited

U.S. PATENT DOCUMENTS

| | | | |
|---|---|---|---|
| 2,406,832 A | | 9/1946 | Hardinge |
| 2,443,363 A | | 6/1948 | Townsend et al. |
| 3,842,825 A | | 10/1974 | Wagner |
| 5,030,220 A | * | 7/1991 | Howland ............... 606/261 |
| 5,269,784 A | * | 12/1993 | Mast ..................... 606/288 |
| 5,306,275 A | * | 4/1994 | Bryan .................... 606/914 |
| 5,364,398 A | | 11/1994 | Chapman et al. |
| 5,462,547 A | | 10/1995 | Weigum |
| 5,527,310 A | | 6/1996 | Cole et al. |
| 5,558,674 A | | 9/1996 | Heggeness et al. |
| 5,704,936 A | * | 1/1998 | Mazel .................... 606/254 |
| 5,766,175 A | | 6/1998 | Martinotti |
| 5,800,162 A | | 9/1998 | Shimodaira et al. |
| 5,964,769 A | * | 10/1999 | Wagner et al. ........... 606/74 |
| 5,975,904 A | | 11/1999 | Spiegel |
| 6,136,002 A | * | 10/2000 | Shih et al. ............... 606/250 |
| 6,296,643 B1 | * | 10/2001 | Hopf et al. ............. 606/263 |
| 6,340,362 B1 | | 1/2002 | Pierer et al. |
| 6,524,315 B1 | * | 2/2003 | Selvitelli et al. ........ 606/70 |
| 6,755,833 B1 | * | 6/2004 | Paul et al. .............. 606/70 |
| 7,094,251 B2 | * | 8/2006 | Bonutti et al. .......... 606/232 |
| 2002/0128653 A1 | | 9/2002 | Haidukewych |
| 2002/0169449 A1 | | 11/2002 | Kuslich et al. |
| 2004/0102778 A1 | | 5/2004 | Huebner et al. |
| 2004/0254577 A1 | * | 12/2004 | Delecrin et al. ........ 606/61 |

(Continued)

FOREIGN PATENT DOCUMENTS

DE    101 17 426    10/2002

(Continued)

*Primary Examiner*—Thomas C Barrett
*Assistant Examiner*—Matthew Lawson
(74) *Attorney, Agent, or Firm*—Maginot, Moore & Beck

(57) ABSTRACT

A bone fixation device comprises a beam including plurality of stacked flexible members. At least one locking member is provided in engagement with the plurality of stacked flexible members. The at least one locking member is configured to retain the plurality of stacked flexible members together in either a locked relationship or an unlocked relationship. In the locked relationship, the at least one locking member compress the plurality of stacked flexible members together. The plurality of stacked flexible members are configured to bend when a threshold force is applied to the beam, provided the plurality of stacked flexible members are in an unlocked relationship. When the plurality of stacked flexible members are in an unlocked relationship, the threshold force is insufficient to bend the plurality of stacked flexible members.

9 Claims, 10 Drawing Sheets

U.S. PATENT DOCUMENTS

| | | |
|---|---|---|
| 2005/0277923 A1 | 12/2005 | Sweeney |
| 2006/0069390 A1* | 3/2006 | Frigg et al. .................... 606/61 |
| 2006/0079892 A1 | 4/2006 | Roychowdhury et al. |
| 2006/0129151 A1* | 6/2006 | Allen et al. .................... 606/69 |
| 2007/0293863 A1* | 12/2007 | Reimels et al. ............... 606/69 |
| 2007/0293864 A1* | 12/2007 | Reimels et al. ............... 606/69 |
| 2008/0015589 A1* | 1/2008 | Hack ........................... 606/69 |
| 2008/0234676 A1* | 9/2008 | Schulze et al. ................ 606/60 |

FOREIGN PATENT DOCUMENTS

| | | | |
|---|---|---|---|
| FR | 2 863 860 | | 6/2005 |
| GB | 2 294 394 | | 5/1996 |
| WO | WO 2007/038429 | * | 9/2006 |
| WO | WO 2007/038429 | | 4/2007 |

* cited by examiner

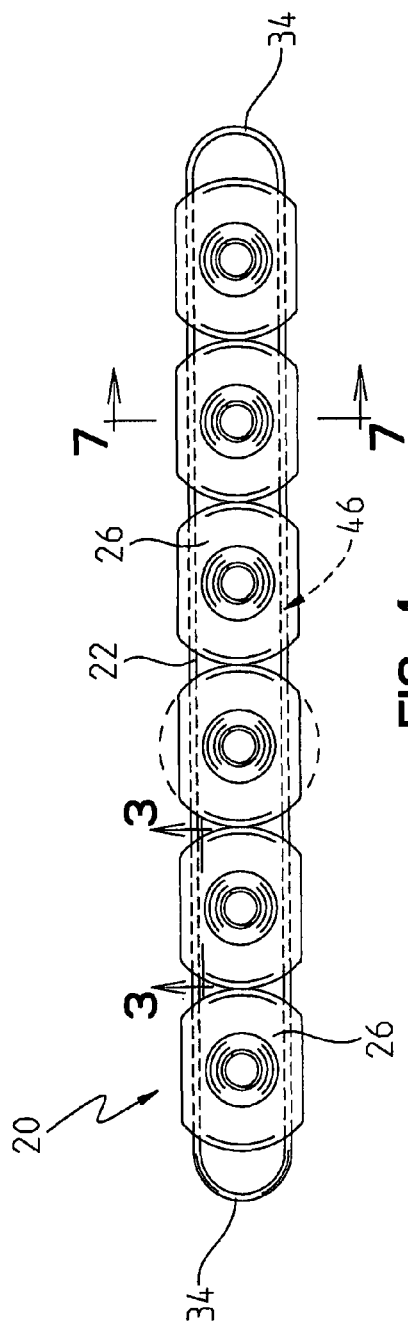
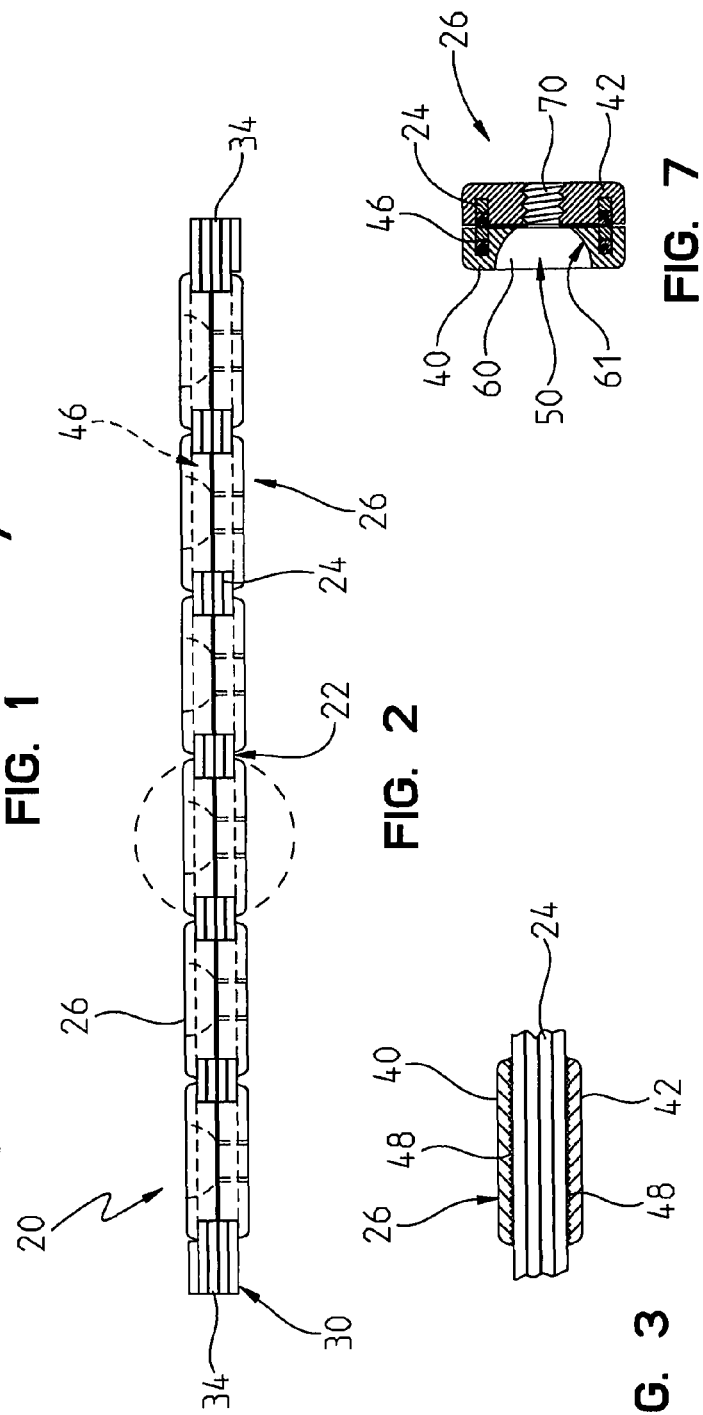
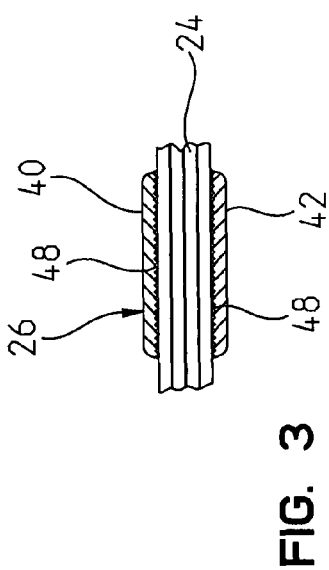
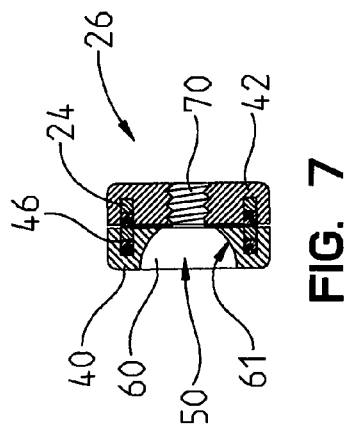
FIG. 1
FIG. 2
FIG. 3
FIG. 7

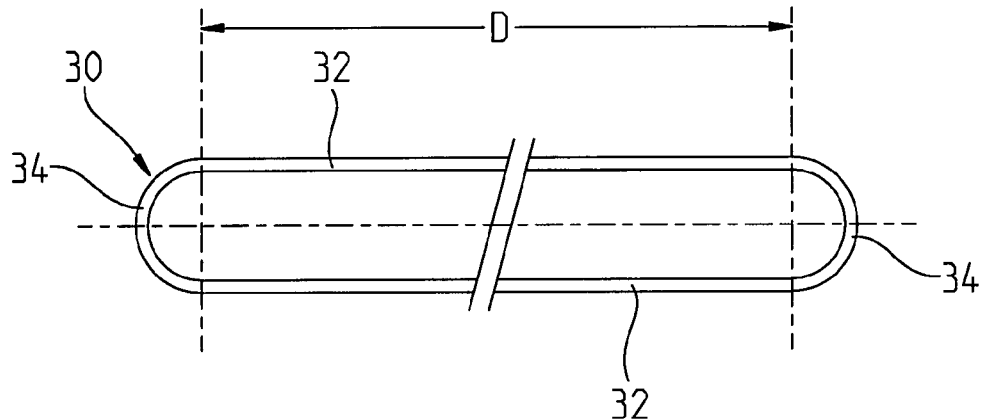
FIG. 4
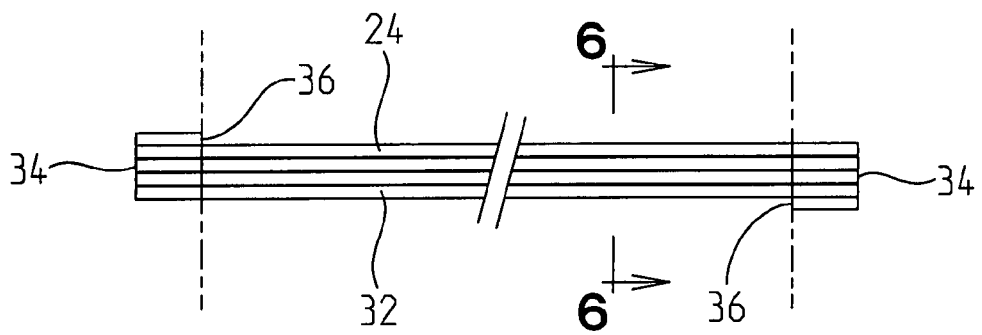
FIG. 5
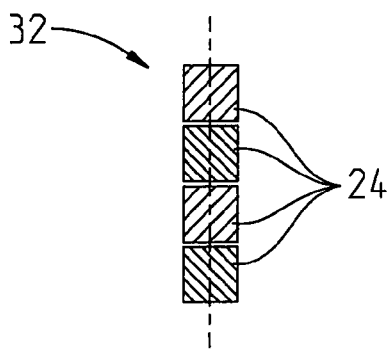 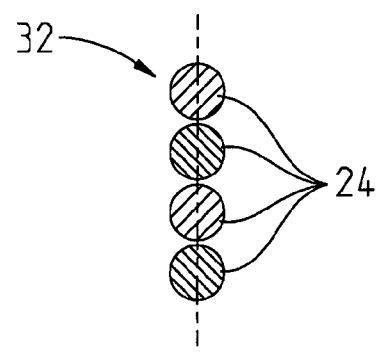
FIG. 6A　　　　FIG. 6B

FLEXIBLE BONE FIXATION DEVICE

FIELD

This application relates generally to the field of orthopedics, and more specifically to bone plates and systems for stabilization and compression of fractured or otherwise damaged bones.

BACKGROUND

Bone plates for internal fixation of fractured bones should generally conform to the contours of the fractured bone surface. This is especially true for compression plates that are screwed tightly against the bone. Matching the plate shape to the bone contours is important with compression plates in order to allow proper distribution of loads between the bone and the plate during healing of the fracture. It is also desirable for the plate to have a low profile and to blend with the bone surface as much as possible so as not to irritate or interfere with surrounding soft tissues, nerves, tendons, vessels, etc.

One type of bone plate for acetabular and other pelvic fractures is called a reconstruction bar. Conventional reconstruction bars are generally formed from a biocompatible metal that may be bent by the surgeon using special tools in order to configure the bar to conform to the bone. Typically the surgeon first forms a thin metal template by hand to conform to the bone surface at the fracture site. Working through an open incision, the surgeon bends the template to approximate the desired shape, places the template against the bone surface, removes the template, adjusts the shape of the template and repeats these steps until the template closely matches the shape of the bone surface. Then the surgeon, sometimes with the help of an assistant, uses a number of special forming tools to bend the reconstruction bar to be implanted into approximately the same configuration as the template, visually holding the bar and template side-by-side to assess when the bar is adequately similar to the template. This procedure may take several minutes of time and a significant amount of skill. The bar may then be attached to the bone using conventional cortical screws. It is not likely that the bar shape exactly matches the bone surface shape, so tightening of the bone screws may draw the bar against the bone surface, thereby inducing bending preloads at various locations along the bar due to the spring-back characteristic of the bar material. Alternatively, the bar may be implanted with significant gaps between various locations of the bar and the bone surface, resulting in the uneven transfer of loads between the bone and bar construct. Therefore, it would be advantageous to provide a reconstruction bar that may be implanted more quickly by the surgeon, requires fewer ancillary tools, is more conformable and contoured to the bone surface and is at least as effective as a fixation device compared to conventional reconstruction bars.

Another issue currently faced by orthopedic device manufacturers is the need to provide a full line of bone plates for a large variety of bone fractures and patient anatomies. The manufacturing costs associated with forming each rigid, one-piece bone plate is significant due largely to the need to configure the plate to approximately match the bone surface shape. Furthermore, a large product inventory must be provided to the user (hospitals) to be prepared for the many types of fractures and patient anatomies to be treated. Accordingly, it would be advantageous to provide bone plates that have broader indications, where each plate may be suitable for a larger variety of fractures and patient anatomies than currently available plates. Potentially, such bone plates may be produced at lower costs than current plates and inventories reduced without compromising surgical outcomes.

SUMMARY

A bone fixation device comprises a beam including plurality of flexible members. The plurality of flexible members extend generally parallel to a curvilinear axis defined along the length of the bone fixation device. The plurality of flexible members are provided in one or more groupings that engage at least one locking member. The locking member is configured to retain the flexible members together in either a locked relationship or an unlocked relationship. In the locked relationship, the locking member compresses the flexible members together. The beam provided by the flexible members is configured to bend when a threshold force is applied to the beam, provided the flexible members are in an unlocked relationship. When the flexible members are in a locked relationship, the beam has an increased resistance to bending such that application of the threshold force is insufficient to bend the plurality of stacked flexible members and alter the shape of the bone fixation device.

In one embodiment, the at least one locking member comprises a first portion configured to engage a first side of the beam and a second portion configured to engage an opposite second side of the beam. The flexible members are arranged within the grouping in a stacked configuration. The first portion and the second portion are configured to clamp together, thus compressing the flexible members. The at least one locking member also comprises a hole extending through the first portion and the second portion. The hole is configured to receive a bone screw configured to draw the first and second portions together to clamp tightly to the flexible members while also securing the bone fixation device to the damaged bone.

The bone fixation device provides for a method of stabilizing a damaged bone. The method comprises providing a plurality of stacked flexible members and at least one locking member. The method further comprises bending the plurality of stacked flexible members to conform surfaces of the bone fixation device to the contours of the damaged bone. After the step of bending, the plurality of stacked flexible members are locked together using the at least one locking member. In particular, the plurality of stacked flexible members are compressed in order to lock the plurality of stacked flexible members together.

The above described features and advantages, as well as others, will become more readily apparent to those of ordinary skill in the art by reference to the following detailed description and accompanying drawings.

BRIEF DESCRIPTION OF THE DRAWINGS

FIG. 1 shows a top view of a bone fixation device including a plurality of locking members and a beam comprised of a plurality of flexible members;

FIG. 2 shows a side view of the bone fixation device of FIG. 1;

FIG. 3 shows a cross-sectional view of one of the plurality of locking members of the bone fixation device of FIG. 1 along line III-III;

FIG. 4 shows a top view of the beam of FIG. 1;

FIG. 5 shows a side view of the beam of FIG. 4;

FIG. 6A shows a cross-sectional view of one embodiment of the beam of FIG. 5 along line VI-VI;

FIG. 6B shows a cross-sectional view of an alternative embodiment of the beam of FIG. 5 along line VI-VI;

FIG. 7 shows a cross-sectional view of one of the plurality of locking members of the flexible bone plate of FIG. 1 along line VII-VII;

DESCRIPTION

Figure 8:
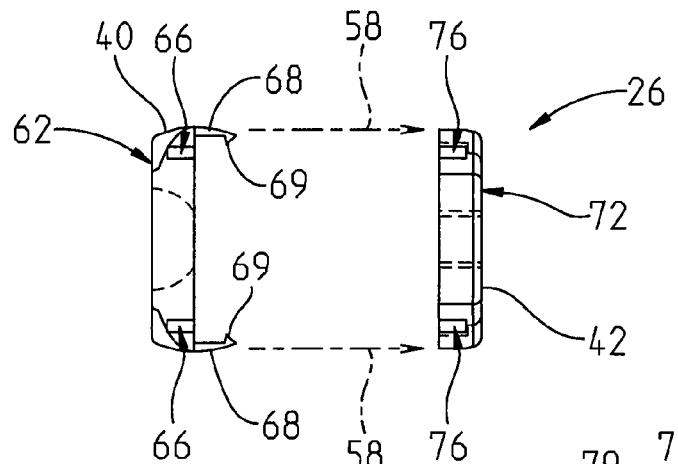
FIG. 8 shows a lateral side view of a top half and a bottom half of one of the plurality of locking members of FIG. 1 in a separated position.
Figure 9A:
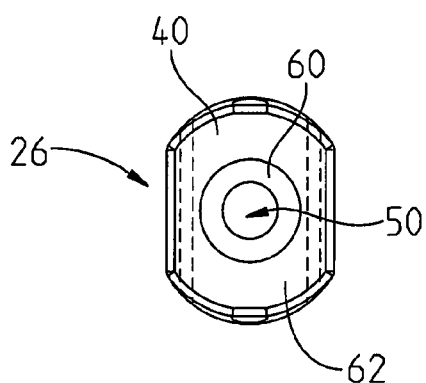
FIG. 9A shows a top view of the top half of the locking member of FIG. 8.
Figure 10A:
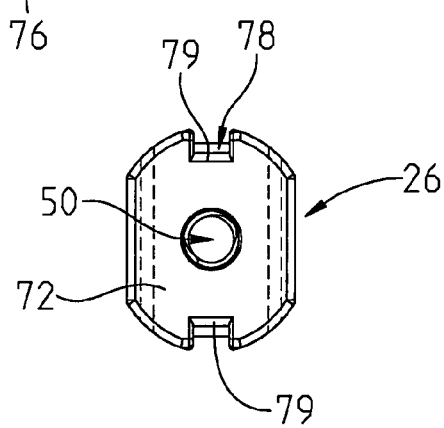
FIG. 10A shows a top view of the bottom half of the locking member of FIG. 8.
Figure 9B:
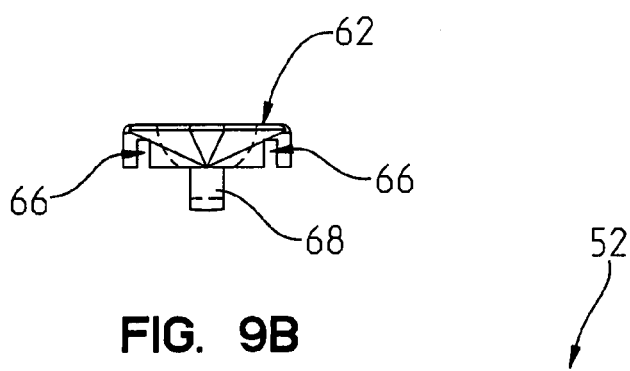
FIG. 9B shows an end side view of the top half of the locking member of FIG. 8.
Figure 10B:
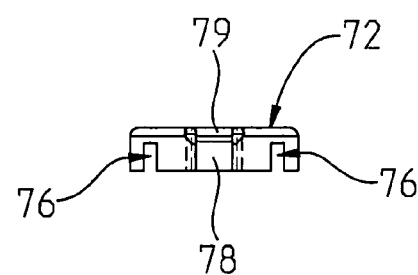
FIG. 10B shows an end side view of the bottom half of the locking member of FIG. 8.

With reference to FIGS. 1 and 2, an embodiment of a bone fixation device 20 is shown. The bone fixation device 20 is a bone plate/reconstruction bar which provides for internal fixation of a fractured bone. The bone fixation device 20 includes a load carrying structure/beam 22 formed from a plurality of flexible members 24. The flexible members 24 are arranged such that the device 20 is in a flexible state when relative movement between the flexible elements is permitted, and in a rigid state when there is substantially no relative movement between the flexible elements. The device 20 further includes at least one locking member 26, whereby the user may apply the locking member 26 to the flexible members 24 in order to change the device 20 between the flexible and rigid states. As explained in further detail below, the device 20 may be easily shaped to conform to the contours of a fractured or otherwise damaged bone surface when the device 20 is in the flexible state. The device may then be converted to the rigid state for fixation of the fractured bone.

As shown in FIGS. 4 and 5, the load carrying beam 22 of the device 20 comprises a plurality of elongate flexible members 24. In the embodiment of FIGS. 4 and 5, the flexible members 24 may be formed from a single filament, such as a metal wire, wound into an oblong coil 30. The oblong coil 30 includes two parallel spaced-apart segments 32 (also referred to herein as groupings 32) having a length D, and two rounded end turns 34 which join the segments 32 and make 180° turns in the coil 30. In this embodiment, the coil terminates in two filament ends 36. The filament ends 36 may bear against the locking members 26 near the rounded end turns 34 of the coil 30.

The filament forming the coil 30 may be formed from a spring steel, a stainless steel, a shape memory metal such as nitinol, titanium alloy, a polymer or other suitable biocompatible material. The cross-sectional shape of the filament forming the coil 30 may be any of numerous cross-sectional shapes. For example, in the embodiment of FIG. 6A, the filament comprising the coil 30 has a rectangular cross-sectional shape, and particularly a square cross-sectional shape. In the embodiment of FIG. 6B, the filament comprising the coil 30 has a rounded cross-sectional shape, and particularly a circular cross-sectional shape. Of course numerous other cross-sectional shaped filaments are possible, including other rectangular wire, such as oblong rectangular, other rounded wire, such as elliptical, and other polygonal shaped wire, such as hexagonal. Alternatively, the flexible members 24 need not be wires, but may be provided my other components, such as a plurality of stacked thin plates. Also, instead of a beam 22 with dual groupings 32, the flexible members 24 may be provided in other configurations, such as a single grouping of flexible members 24, or two or more unconnected groupings providing separate beams.

As shown in FIGS. 5-6B, the elongated flexible members 24 are vertically stacked or layered in each grouping 32. An equal number of flexible members 24 are provided in each stack, such that the sum of the thicknesses (or diameters) of the flexible members 24 is the overall thickness of the load carrying structure 22. While only a single stack of flexible members 24 is shown in FIGS. 6A and 6B, two or more side-by-side stacks of flexible members may be provided in alternative embodiments.

In other embodiments, the flexible members 24 may also be arranged within each grouping in configurations other than vertical stacks. For example, the flexible members 24 may be held together in a bundled configuration having an approximately circular cross-sectional shape (not shown).

With reference again to FIGS. 1 and 2, the bone fixation device 20 also includes a plurality of locking members 26 are arranged upon the beam 22. In the disclosed embodiment, six locking members 26 are aligned end-to-end, although it is possible to have fewer or many more locking members 26, as desired. Each locking member 26 includes a top half 40 and a bottom half 42, which may be loosely attached together, such as by an integral latching element 44 (see FIG. 8). When the top half 40 and the bottom half 42 are joined, two channels 46 are formed extending through the locking member 26. The channels 46 are represented in FIGS. 1 and 2 by the dotted lines that extend through each locking member 26 between the exposed portions of the beam 22. The channels 46 in each locking member 26 provide a passage allowing the plurality of flexible members 24 of the beam 22 to extend through the locking member 26, with separate halves 40, 42 of the locking member provided on opposite sides of the beam 22. Each locking member 26 is comprised of a biocompatible material, such as, for example, metal injection molded (MIM) 316L stainless steel or any one of numerous other biocompatible metals or materials, as will be recognized by those of skill in the art.

Figure 11:
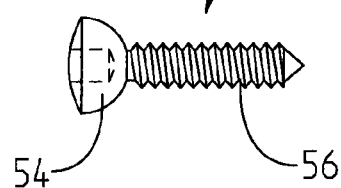
FIG. 11 shows a bone screw configured for insertion through the locking member of FIG. 8.

With reference to FIG. 7, each locking member 26 includes a bone screw hole 50 that extends through the top half 40 and the bottom half 42 of the locking member. The top half 40 of the locking member 26 includes a recess 60 that provides a concave surface 61 for receiving the head of a bone screw. The recess 60 also allows the threaded shaft of a bone screw to pass freely through to the bottom half 42. An exemplary bone screw 52 is shown in FIG. 11 and includes a head 54 with a threaded shaft 56 extending from the head 54. The bottom half 42 of the locking member 26 includes a threaded portion 70 configured to threadedly engage the threaded shaft 56 of the screw 52. When the screw 52 is inserted into the hole 50, the threaded shaft 56 passes through the top half 40 of the locking member and engages the threaded portion 70 of the bottom half 42. Then, when the screw 52 is tightened, the bottom half 42 is drawn tightly against the top half 40 of the locking member 26, thereby locking the screw in the segment. Alternately, the bottom half 42 of the locking member may include an unthreaded clearance hole for the bone screw 52, such that when the bone fixation device 20 is attached to the bone using the bone screw 52, the compression against the bone surface causes the top and bottom halves to clamp together. At the same time, the bone screw serves as a fastener to attach the bone fixation device to the bone.

With reference now to FIGS. 8-10B, one embodiment of a locking member 26 is shown with the top half 40 separated from the bottom half 42. The top half 40 includes a generally planar upper surface 62 with the recess 60 leading to the hole 50 formed therein. A sidewall 64 extends from the edges of the upper surface 62 toward the bottom half 42. Slots 66 are formed within the sidewall 64 to provide for the channels 46 that extend through the locking member 26. Tabs 68 extend from the sidewall 64 toward the bottom half 42 of the locking member 26. The tabs 68 include teeth 69 on their ends that are designed to engage the bottom half 42 of the locking member and secure the top half 40 to the bottom half 42.

The bottom half 42 of the locking member 26 includes a generally planar lower surface 72 with the hole 50 extending through the lower surface 72. A sidewall 74 extends from the edges of the lower surface toward the top half 40. Slots 76 are formed within the sidewalls 74 to provide for the channels 46 to extend through the locking member 26. Grooves 78 are formed in the sidewalls 74 to receive the tabs 68 of the top half 40 of the locking member. In particular, the teeth 69 of the tabs 68 are configured to engage shelves 79 in the grooves 78 of the bottom half 42, thus loosely securing the top half to the bottom half. The arrows 58 in FIG. 8 indicate the orientation and direction in which the two halves 40, 42 may be snapped together to secure the two halves together. When the two halves 40, 42 of the locking member 26 are joined together, the slots 66 and 76 on the two halves are aligned and form openings to the channels 46 in the locking member 26. Thus, the locking member 26 may be secured to the beam 22 with the plurality of flexible members 24 extending through the channels 46 of the locking member and out the slots 66, 76.

Figure 15:
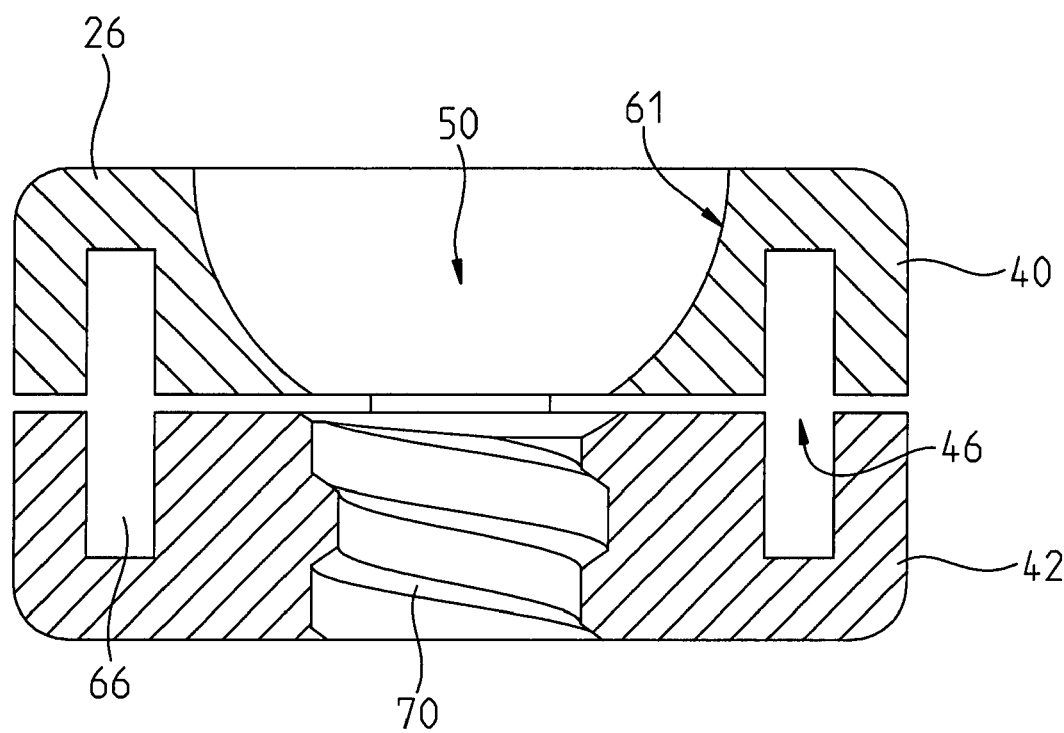
FIG. 15 shows a cross-sectional view of the locking member of FIG. 14.
Figure 16:
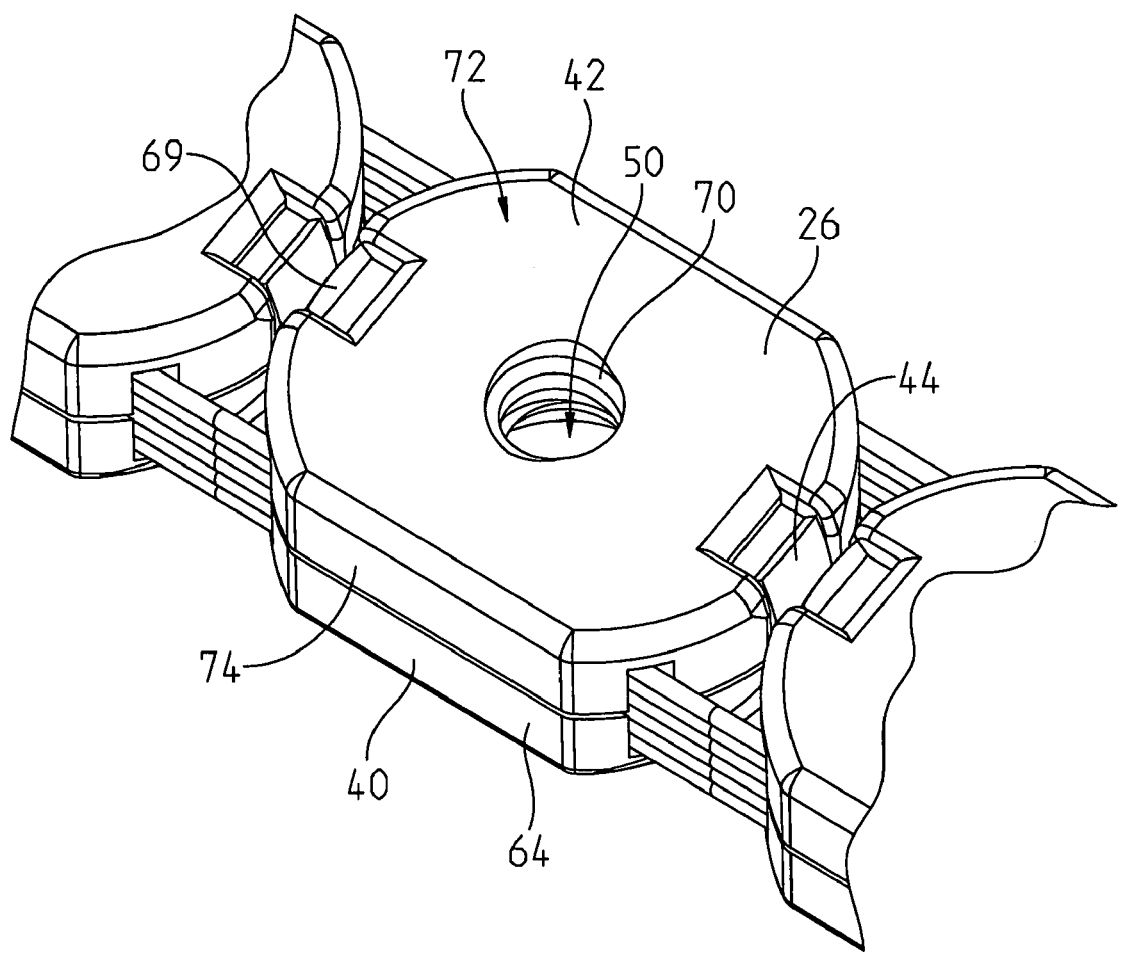
FIG. 16 shows a lower perspective view of the locking member of FIG. 14.

The channels 46 formed through a locking member 26 may include features to help maintain the locking member 26 in place upon the beam 22. For example, as shown in FIG. 3, each channel 46 may include a pair of opposing, serrated clamping surfaces 48 to help prevent movement of the flexible members 24 in the channels 46 when the bone screws are tightened. Accordingly, the serrated clamping surfaces 48 are provided to assist in preventing relative movement between the flexible elements and facilitate locking the bone fixation device 20 into a rigid condition. The serrated clamping surfaces may be provided by a ribbed, toothed or other textured surface. The channels 46 may be provided in different cross-sectional shapes dependant on the shape of the beam 22. Thus, while the channels 46 are shown with a rectangular cross-section in FIG. 7 (and FIG. 15), the channels 46 could also have a different cross-sectional shape. For example, if the beam 22 were provided as a plurality of flexible members 24 arranged in a bundled configuration, the cross-sectional shape of the channels 46 may be circular.

Figure 12A:
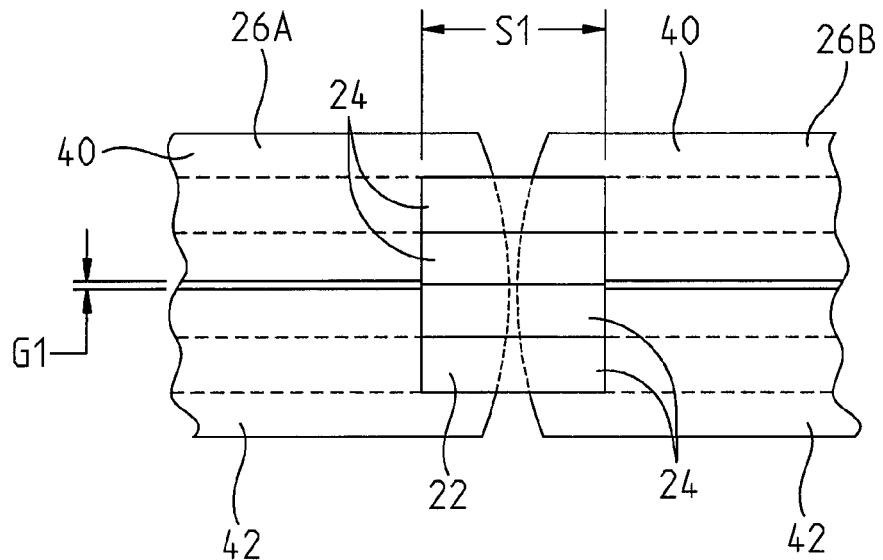
FIG. 12A shows a lateral side view of two of the plurality of locking members of FIG. 1 in an unlocked configuration.

FIG. 12A shows a detailed side view of a portion of a pair of adjacent locking members 26A, 26B with a portion of the beam 22 extending between the locking members 26A, 26B. In the embodiment of FIG. 12A, the beam 22 includes four stacked flexible members 24. When the top half 40 of the locking member 26A is loosely connected to the bottom half 42 (i.e., before tightening of the bone screw), the portion of the four flexible elements between the segments may be characterized as four individual segments having a length of S1. A gap G1 exists between the top half 40 and the bottom half 42 of the locking member 26A. This gap G1 provides a distance over which the clamping surfaces of the channels 46 of the locking member 26A may apply a clamping force on the flexible members 24.

Figure 12B:
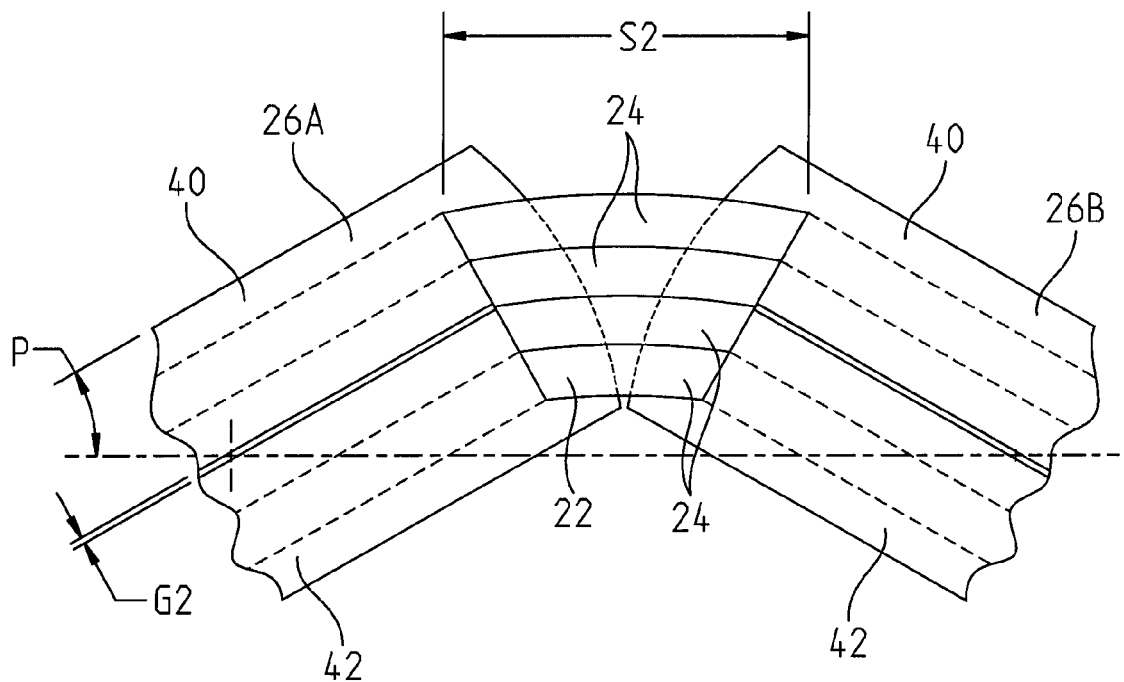
FIG. 12B shows a lateral side view of two of the plurality of locking members of FIG. 1 in a locked configuration.
Figure 13:
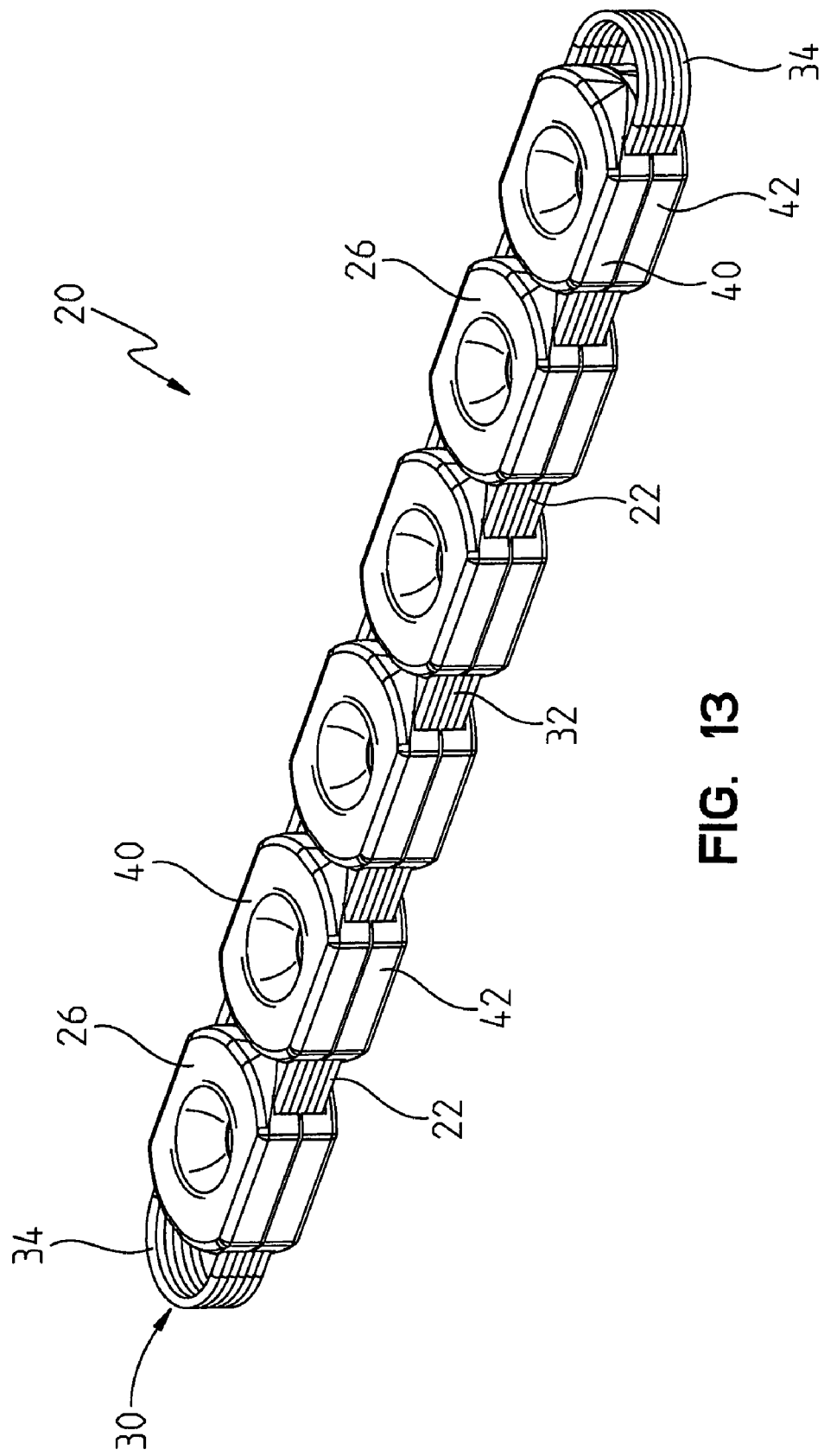
FIG. 13 shows a perspective view of an alternative embodiment of the flexible bone fixation device of FIG. 1.
Figure 14:
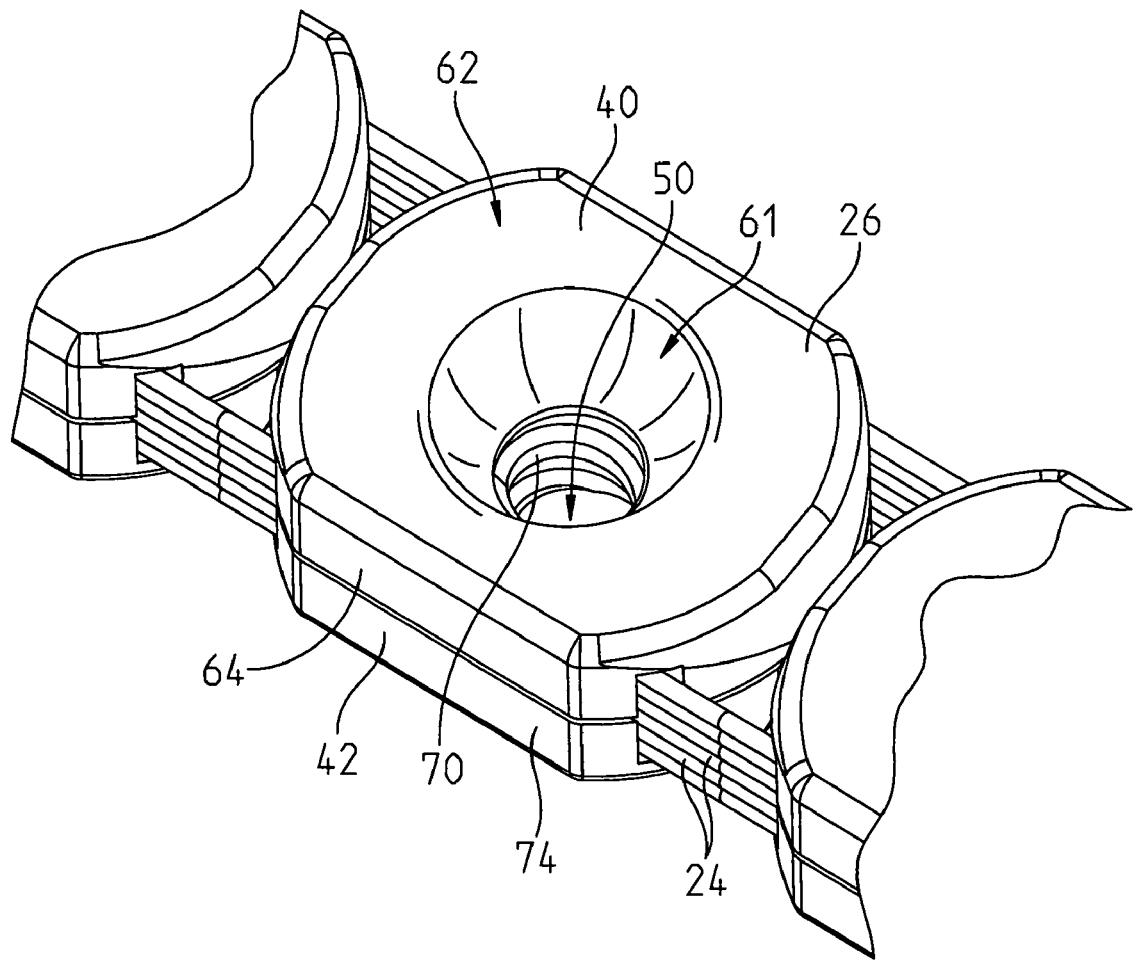
FIG. 14 shows an upper perspective view of one of the locking members of the flexible bone fixation device of FIG. 13.

FIG. 12B shows the same adjacent locking members 26A, 26B, as FIG. 12A. However, in FIG. 12B, the locking members 26A, 26B are angled relative to one another. Such angling may be necessary when the bone fixation device 10 is positioned on a contoured bone surface. In this position, the exposed portion of the flexible members 24 between the locking members 26A, 26B is generally trapezoidal in shape with a maximum dimension of S2>S1. This angled positioning between locking members 26A, 26B may be achieved when a threshold force is applied to one of the locking members 26A, 26B, thus moving the one locking member 26A relative to the other locking member 26B. The flexible quality of each of the individual flexible members 24 is defined by a moment of inertia (i.e., second moment of area) and the elasticity of the material comprised in the flexible members 24. Because of the relatively loose relationship between the flexible members, the threshold force required to bend the beam 22 is approximately equal to the aggregate bending stress for each of the plurality of flexible members 24.

When a bone screw is placed in the hole 50 of each locking member 26A, 26B, and used to compress the top half 40 of each locking member 26 toward the bottom half 42, the plurality of flexible members 24 are also compressed together. The plurality of flexible members 24 only permit a certain amount of compression, such that a gap G2 (G2<G1) still exists between the top half and the bottom half following compression by the bone screw. With the top half 40 and bottom half 42 of each locking member 26A, 26B clamping down on the flexible members 24, the flexible members 24 are fixed together and not permitted to move relative to each other, thereby greatly increasing the stiffness of the beam 22 at that location. Accordingly, the threshold force that would formerly cause the first locking member 26A to move relative to the second locking member 26B is no longer sufficient to bend the beam 22, and a much greater force is required to move the first locking member 26A relative to the second locking member 26B. This locking feature allows the flexible bone plate 20 to be bent by the hands of a human in the unlocked position by adjusting the position of adjacent locking members 26, while preventing the bone from being bent by the hands of a human in the unlocked position.

As set forth in the preceding paragraph, the beam 22 in the bone plate 20 has one measure of stiffness in an unlocked position and a different measure of stiffness in an unlocked position. In general, the strength of any beam is a function of a beam stiffness factor associated with each mode of beam loading/deflection. The stiffness factor may be defined as the product of the modulus of elasticity E of the beam material times the moment of inertia I about the neutral axis in the direction of the beam deflection. Given a beam material, a comparison of the moments of inertia for the proposed and conventional reconstruction bars may help predict the usefulness of the proposed material as a flexible member 24 for the beam 22 in the disclosed bone plate 20. For example, if a one-millimeter square wire is used to form each flexible member 24, the sum of the individual bending moments of inertia about the neutral axis of the four beams in the vertical direction is about 0.33 mm$^4$. Using such wire for the beam described for FIGS. 12A and 12B, the bending moment of inertia of the beam 22 in the locked position shown in FIG. 12B would be about 5.33 mm$^4$, or 16 times the stiffness of the arrangement described for FIG. 12A. Since the beam 22 has a pair of spaced apart bundles of flexible members 24 (i.e., the coil 30 provides two beams 22 with each beam extending through the locking members 26), the overall bending moment of inertia in the vertical (up-and-down) direction (shown in FIG. 12B) is twice that of the single beam (i.e., 10.66 mm$^4$ rather than 5.33 mm$^4$). In the transverse (side-to-side) direction, a pair of spaced-apart laminated beams as shown in FIG. 12B has an overall bending moment of inertia of about 333 mm$^4$.

FIGS. 13-16 show numerous views of an alternative embodiment of the bone fixation device shown in FIGS. 1-12. In the embodiment of FIGS. 13-16, the beam 22 comprises six flexible members 24 rather than the four flexible members shown in FIGS. 1-12. The six flexible members 24 in FIGS. 13-16 are formed from 0.50 mm wire wound in a coil 30 to provide a grouping having six layers of flexible members 24. The spacing between the centers of the screw holes 60 in each locking member 26 is about 16.7 mm (0.625 inch). The screw holes are sized for receiving standard, 5 mm cortical bone screws.

Figure 18:
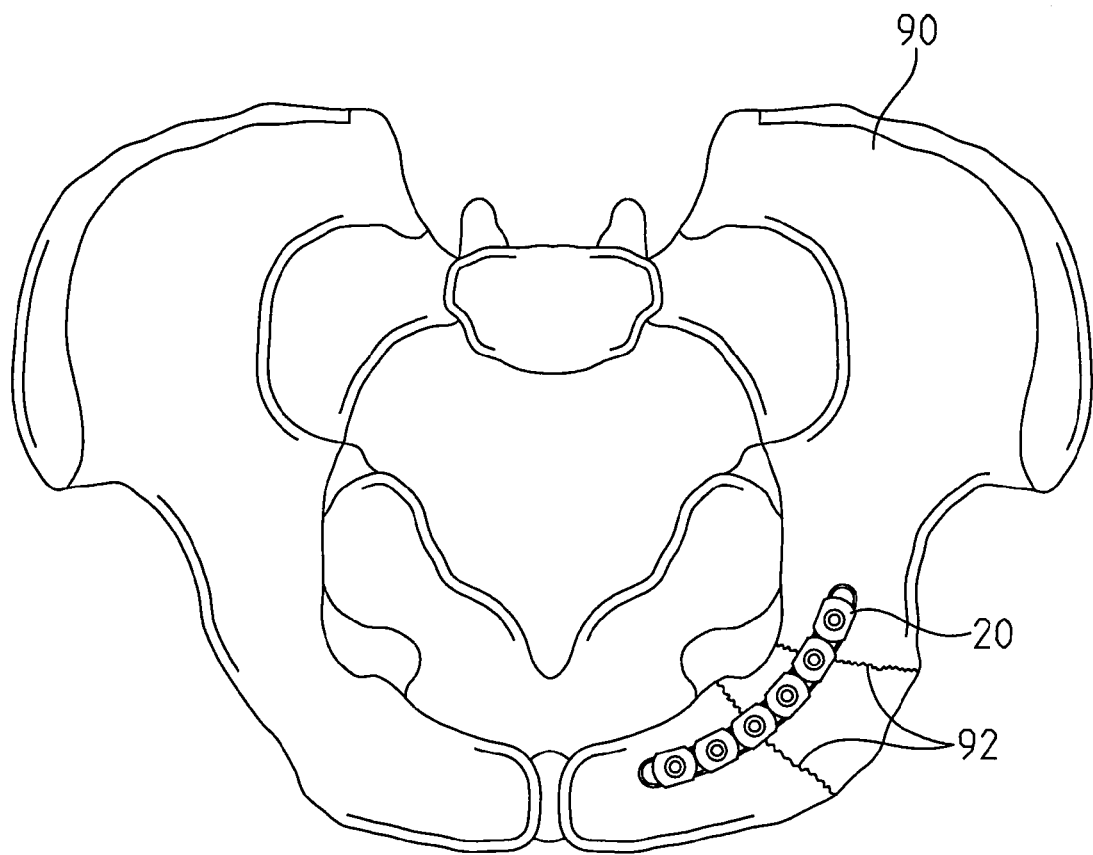
FIG. 18 shows an anterior view of a portion of a human pelvis, showing the bone fixation device of FIG. 1 attached to the pelvis.

In operation, the flexible bone fixation device 20 is configured for attachment to a fractured or otherwise damaged bone. FIG. 18 shows the bone fixation device 20 positioned upon a human pelvis 90. The bone fixation device 20 extends over the fractures 92 in the pelvis. When positioning the bone fixation device 20 upon the pelvis, the surgeon first clears the tissue from the fracture to expose the bone. Next, the surgeon places the bone fixation device 20 on the bone with the plurality of flexible members 24 in the unlocked relationship and the bone fixation device spanning across the fracture 92. The surgeon presses on the bone fixation device, applying bending forces to the appropriate locations on the bone fixation device such that the bone fixation device generally conforms to the contours of the bone and is curved or otherwise conformed to a desired shape. Accordingly, the bone fixation device may be bent in three dimensions (i.e., vertical bends, lateral bends, as well as twisting bends). Bending of the bone fixation device 20 may also be envisioned in relation to a curvilinear axis that extends along the length of the bone fixation device 20 generally parallel to the beam 22. Accordingly, the beam 22 may be bent laterally (side-to-side) relative to the curvilinear axis, vertically (up-and-down) relative to the curvilinear axis, or twisted about the curvilinear axis.

After the bone fixation device 20 is bent to the desired shape, the surgeon then starts the process of securing the bone fixation device to the bone. Starting at one end of the bone fixation device, the surgeon uses the holes 50 in the locking members 26 as a guide to drill a hole in the bone. The surgeon then inserts a bone screw through the hole and into the bone. When the bone screw is tightened in the locking member 26, the locking member compresses the plurality of flexible members together, placing the plurality of flexible members in a locked relationship at that location along the curvilinear axis of the bone fixation device 20. The surgeon follows this procedure to the opposite end of the bone fixation device until all of the locking members secure the plurality of flexible members in a locked relationship, and the bone screws are fixed to the bone. Alternatively, the surgeon may fully insert a bone screw in a hole in the middle of the bone fixation device 20 and proceed to fully insert the next bone screw in an adjacent hole in either direction, until all the screws are fully inserted. Furthermore, in some surgical applications, it may be desirable to partially insert all the bone screws into the holes of the fixation device 20, and then to tighten each screw starting from either end of the device 20, or the middle of the device 20. For each of the above-described procedures, it is generally desirable to position each locking member against the bone surface prior to fully tightening the bone screw through the locking member. However, there may be some surgical situations where the surgeon prefers to attach the fixation device to the bone surface with a gap between the bone surface and at least some of the locking members.

With the above described procedure, a bone fixation device is provided that is easily bent to match the contours of the bone surface. The forces required to bend the bone plate may be provided by the human hand. Because the bone fixation device is easily shaped, and no tools are required to bend the bone fixation device, the time needed to perform the surgical procedure installing a bone fixation device is reduced. In addition, because a single bone fixation device may be bent into numerous shapes, there is a reduced need to have bone fixation devices of various shapes on hand, and hospital inventories of bone fixation devices may be reduced.

Figure 17:
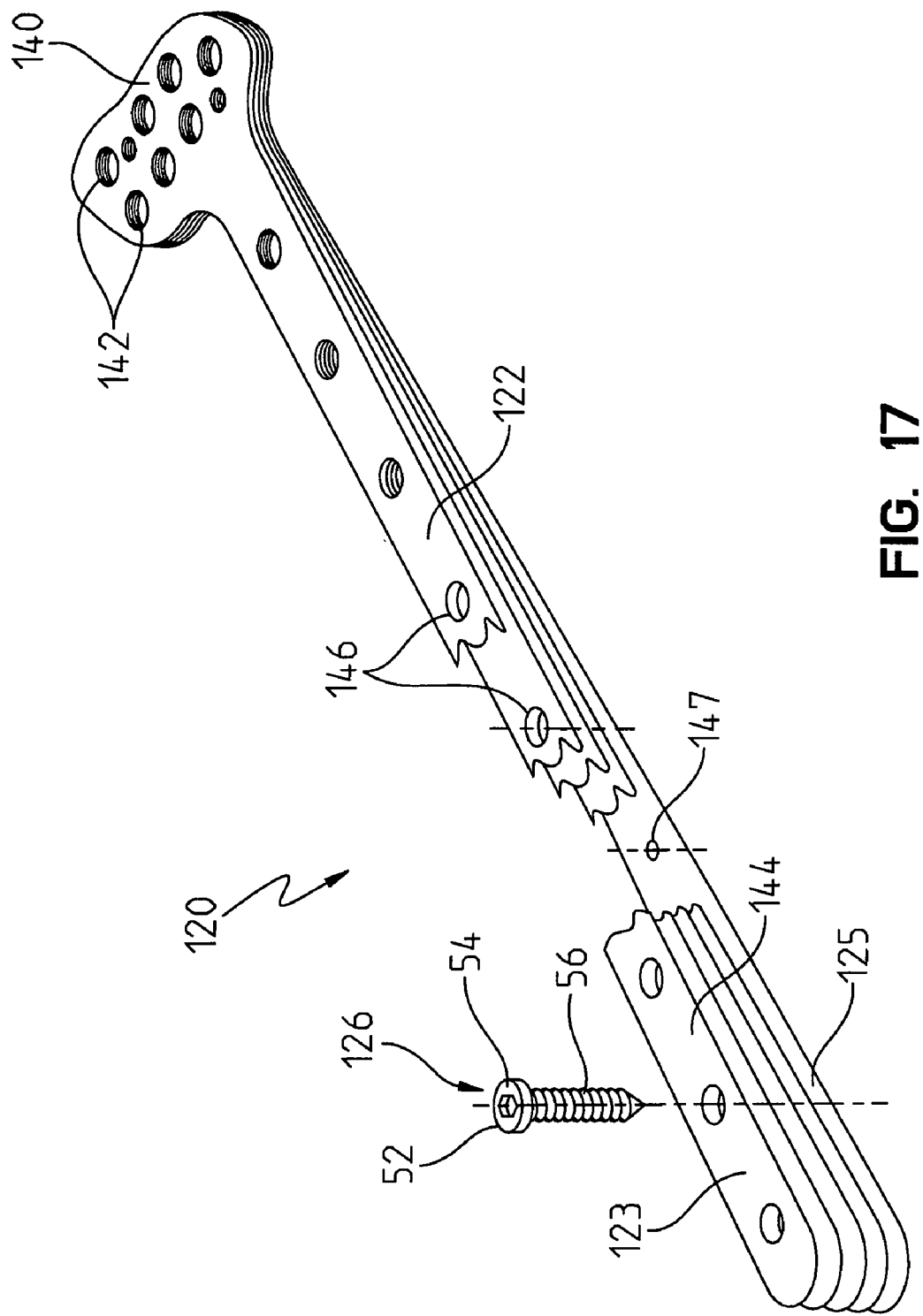
FIG. 17 shows a perspective view of an alternative embodiment of the flexible bone fixation device of FIG. 1.

FIG. 17 shows another alternative embodiment of a bone plate 120 that may be applied as a bone fixation device for fixation of various bones, such as the proximal humerus. As in the above-described embodiments, the bone fixation device 120 includes a load carrying structure formed from a plurality of flexible members 124. The flexible members 124 are provided as a plurality of elongated laminates formed from thin sheets of a biocompatible metal, polymer, fabric, paper, absorbable material, or other suitable material.

In the embodiment of FIG. 17, the bone fixation device 120 includes a head portion 140 and a stem portion 144. The laminates 124 may be partially joined near the head end, such as by welding, cementing, etc., in order to keep the laminates in general alignment. However, in other embodiments the laminates 124 may be initially separated from each other. The head portion 140 includes a plurality of holes 142 that extend through the laminates. Each of the plurality of holes 142 are configured to receive one of the locking members 126, such as, for example, a polyaxial locking screw 52, a non-locking screw, a guidance wire, a suture, or other locking member.

The stem portion 144 of each laminate 124 also includes a plurality of holes 146. The holes 146 in each laminate layer are aligned to allow a bone screw or other fixation device to pass through the aligned holes. The laminates 124 on the stem portion 144 may be initially provided with or without the stem holes 146.

If holes 146 are not initially provided in the stem portion 144, the surgeon may drill each hole through the laminates 124 and into the bone in a single step. However, before drilling any hole 146 the surgeon first presses the portion of the laminates that will receive the hole against the bone surface to properly bend the laminates into alignment with the bone. In this embodiment, the upper flexible member, such as laminate 123 in FIG. 17, may also include small pilot holes to guide the tip of the drill. The surgeon applies spaced-apart screws in this manner, proceeding from a location near the head of the plate, and moving towards the opposite end. After drilling each hole, the surgeon inserts a screw through the hole, thereby locking the laminates together at that location and attaching that portion of the plate to the bone.

Alternatively, if the holes 146 are initially provided in the stem portion 144, the holes 146 are spaced apart according to a pre-determined configuration. In this embodiment, the holes 146 in the bottom flexible member 124 that contacts the bone surface, such as hole 147 in laminate 125 shown in the cutaway portion of FIG. 17, may be sized for guiding the bone drill and for locking engagement with the thread of a cortical bone screw. The holes 146 in the other flexible members 124 above the bottom laminate 125 may be significantly larger than the major diameter of the bone screw thread. In one embodiment, the holes are successively larger in each laminate layer above the bottom laminate 125. In particular, the head of the bone screw will generally have a larger diameter than the smallest diameter of the larger holes on the upper laminate layer. This arrangement allows the flexible members to be bent while still allowing the pre-drilled holes 146 to remain in sufficient alignment to allow a bone screw to pass through the holes 146. Specifically, when the flexible members 124 are bent, the position of a hole 146 in the top laminate 123 will shift to a different extent than a hole in the bottom laminate 125. However, the holes 146 in the upper laminates are sufficiently larger than holes in the lower laminate 125 such that a passage remains through the holes that will accept a bone screw, despite the slightly shifted/offset position of the holes relative to one another. In this embodiment, the holes in the laminates 124 may be circular or elongated in the form of slots. In particular, elongated slots in the upper laminates are advantageous to ensure hole alignment following bending of the bone fixation device.

With pre-formed holes in the bone fixation device 120, the surgeon begins attaching the device 120 to the bone starting at the set of holes near the head 140 of the bone fixation device 120. The surgeon pushes the laminates 124 against the bone surface at that location and use the smaller hole 146 in the bottom laminate 125 to guide the bone drill. The surgeon may then immediately insert a bone screw through all the laminates at that location and tighten the screw, thereby locking the laminates together at that location. The surgeon may then proceed to the next hole location and repeat the procedure until all the screws are in place. As described above, the upper laminate holes provide significant clearance for the screw threads while the holes in the bottom laminate 125 are configured to engage the screw threads. Although the laminates may shift with respect to each other as the surgeon shapes the plurality of flexible members to conform to the bone contours, the differently sized holes still allow for passage of the bone screw. Once the bone screws are tightened, compressing the laminates 124 against the bone, the beam 122 is in the rigid/locked condition and configured for fixation of the bone fracture.

The laminates 124 shown in FIG. 17 may be made from any one of numerous materials including metals and polymers, and may be adhered together, at least provisionally until screws are inserted, with a biocompatible bonding agent such as cyanoacrylate cement or bone cement. The laminates may also be formed form a metallic mesh material which provides numerous holes in each layer. By using such a mesh material, it is not necessary to drill holes into the laminates, and the holes in the mesh may provide for passage of the bone screw through the laminates.

In other embodiments, the laminates 124 of the bone fixation device 120 of FIG. 17 may be formed from different materials that provide additional features and benefits. For example, the bottom laminate 125 may be made of a resilient material such as silicone rubber to provide a conformable interface against the bone surface, thereby helping to preserve blood flow in the periosteum. Alternatively, the bottom laminate 125 may be formed from an absorbent material such as a sterile cotton fabric containing a therapeutic agent such as an antimicrobial to help prevent infection of tissues at the wound site. Intermediate laminates may be made of materials design to augment the flexibility, hardness, fatigue resistance, and other mechanical properties, thereby forming a composite flexible bone plate with improved properties.

In one embodiment, the laminates 124 of FIG. 17 may be cut to length during the surgical procedure. For example, the flexible bone plate 120 shown in FIG. 17 may be provided with an extra long stem 144 to accommodate an extremely large patient. The surgeon may then use surgical shears to cut each laminate 124 to the desired length. In this way the surgeon may also stair step or taper the end of the stem to more nearly resemble the formation of natural callus over the fracture. In one embodiment, a roll of laminate may be provided such that the surgeon may cut a desired number of flexible elements from the roll, align them in a vertically layered configuration, and attach them to the bone. The rolled laminate may include an adhesive for provisional placement of the layers until the screws are tightened against the bone. The laminates may also be provided in sheet form rather than strips. Many other variations of laminates, flexible members, plates and related methods of using such members may be envisioned by those skilled in the art.

In the above-described embodiments, the surfaces of the flexible members or laminates may be treated or provided with any one of numerous processes, coatings, or features to enhance the frictional lock achievable when fixed together in the rigid condition. For example, the surfaces of the flexible members may be provided with a rough texture, such as may be obtained by sand blasting, or a multiplicity of tiny projections, teeth, serrations, or other structural features. A bonding agent such as a moisture activated cement or glue may be coated or otherwise disposed on the surfaces of the flexible members, such that once the implant is placed in the wet environment of the body, the bonding agent becomes active, and cures fully several minutes or hours later to increase the rigidity of the construct. The bonding agent may also be activated by heat, UV radiation, or other energy source.

Although the present invention has been described with respect to certain preferred embodiments, it will be appreciated by those of skill in the art that other implementations and adaptations are possible. For example, although the flexible members disclosed herein have been shown stacked in a vertical fashion, the flexible members may also be positioned laterally relative to one another. In addition, the shapes of the locking members and the flexible members may vary according to the desired surgical application. For example, the locking members 26 shown in FIG. 1 may be longer, wider, circular, T-shaped, L-shaped, or shaped otherwise such that the bone fixation device may be better adapted to match the patient's anatomy. Or, for example, the fixation device 120 shown in FIG. 17 may be provided without a head portion, such that the device is more appropriate for fixation of a long bone fracture. Of course, numerous other adaptations are possible. Moreover, there are advantages to individual advancements described herein that may be obtained without incorporating other aspects described above. Therefore, the spirit and scope of the appended claims should not be limited to the description of the preferred embodiments contained herein.

What is claimed is:

1. A bone fixation device comprising:
   a) a beam comprising plurality of flexible members, wherein the plurality of flexible members are configured to bend when a threshold force is applied to the beam and the plurality of flexible members are in an unlocked relationship; and
   b) a plurality of locking members configured to compress the plurality of flexible members together and into a locked relationship, wherein the threshold force applied to the beam is insufficient to bend the plurality of flexible members in the locked relationship;

wherein each locking member in the plurality includes a top portion and a bottom portion, the top portion and the bottom portion of each locking member cooperating to define a first channel and a second channel;

wherein the plurality of locking members are arranged end to end such that the first channels of each locking member are aligned to form a first passage and the second channels of each locking member are aligned to form a second passage;

wherein the plurality of flexible members of the beam comprise filaments arranged in a first stacked grouping and a second stacked grouping, the first stacked grouping being positioned in the first passage and the second stacked grouping being positioned in the second passage;

wherein the top portion and the bottom portion of each locking member are configured to move between a first relative position and a second relative position with respect to each;

wherein, in the first relative position, the top portion and the bottom portion are spaced apart from each other a distance so that the filaments of the first stacked grouping and the second stacked grouping are in an unlocked relationship in which the filaments of the first stacked grouping are able to move with respect to each other in the first channel and the filaments of the second stacked grouping to move with respect to each other in the second channel, respectively;

wherein, in the second relative position, the top portion and the bottom portion of the locking members are positioned with respect to each other to compress the filaments of the first stacked grouping together in the first channel and into the locked relationship and to compress the filaments of the second stacked grouping together in the second channel and into the locked relationship such that the filaments of the first stacked grouping and the second stacked grouping are prevented from moving with respect to each other.

2. The bone fixation device of claim 1 wherein the plurality of flexible members have a rectangular cross-sectional shape.

3. The bone fixation device of claim 1 wherein the plurality of flexible members have a rounded cross-sectional shape.

4. The bone fixation device of claim 1 wherein the at least one locking member comprises a first portion configured to engage a first side of the first stacked grouping and a first side of the second stacked grouping and a second portion configured to engage a second side of the first stacked grouping and a second side of the second stacked grouping, wherein the first portion and the second portion are configured clamp the first stacked grouping and the second stacked grouping.

5. The bone fixation device of claim 4 wherein each locking member in the plurality of locking members includes a hole extending through the first portion and the second portion, wherein the hole is configured to receive a bone screw.

6. The bone fixation device of claim 5 wherein the hole of each locking member in the plurality includes a clearance hole extending through the first portion and a threaded hole extending through the second portion, the clearance hole configured to freely pass a bone screw and the threaded hole configured to threadedly engage the bone screw, wherein tightening the bone screw in the hole draws the first portion and the second portion together to compress the plurality of flexible members.

7. The bone fixation device of claim 1 wherein the plurality of flexible members comprises at least three flexible members.

8. The bone fixation device of claim 1 wherein the beam defines a curvilinear axis for the bone fixation device, and wherein application of the threshold force bends the beam in an up-and-down direction relative to the curvilinear axis when the flexible members are in the unlocked relationship.

9. The bone fixation device of claim 1 wherein the beam defines a curvilinear axis for the bone fixation device, and wherein application of the threshold force bends the beam about the curvilinear axis when the flexible members are in the unlocked relationship.

* * * * *